United States Patent
Kazimierski

(10) Patent No.: US 8,575,349 B2
(45) Date of Patent: Nov. 5, 2013

(54) DERIVATIVES OF 1-ALKYL-6-OXO-PIPERIDINE-3-CARBOXYLIC ACIDS AND 1-ALKYL-5-OXO-PYRROLIDINE-3-CARBOXYLIC ACIDS AND THEIR USES AS COOLING COMPOUNDS

(75) Inventor: Arkadiusz Kazimierski, Old Bridge, NJ (US)

(73) Assignee: International Flavors & Fragrances Inc., New York, NY (US)

( * ) Notice: Subject to any disclaimer, the term of this patent is extended or adjusted under 35 U.S.C. 154(b) by 125 days.

(21) Appl. No.: 12/951,173

(22) Filed: Nov. 22, 2010

(65) Prior Publication Data

US 2012/0129827 A1    May 24, 2012

(51) Int. Cl.
*C07D 401/06* (2006.01)
(52) U.S. Cl.
USPC .......... 546/208; 424/46; 424/78.03; 540/602; 546/188; 548/518; 548/519; 548/591; 548/953
(58) Field of Classification Search
USPC .......... 424/46, 78.03; 540/602; 546/188, 208; 548/518, 519, 591, 953
See application file for complete search history.

(56) References Cited

FOREIGN PATENT DOCUMENTS

WO    WO2012048775    *    4/2012

OTHER PUBLICATIONS

Buzas et al. "Synthesis . . . " CA78:43180 (1973).*
Schopohl, et al., "Synthesis and Characterization of Enantiomerically Pure Menthylamines and their Isocyanates" Synthesis 2003(17): 2689-2694.

* cited by examiner

*Primary Examiner* — Celia Chang
(74) *Attorney, Agent, or Firm* — Elizabeth M. Quirk; XuFan Tseng; Joseph F. Leightner

(57) ABSTRACT

The present invention relates to novel derivatives of 1-alkyl-6-oxo-piperidine-3-carboxylic acids and 1-alkyl-5-oxo-pyrrolidine-3-carboxylic acids represented by Formula I:

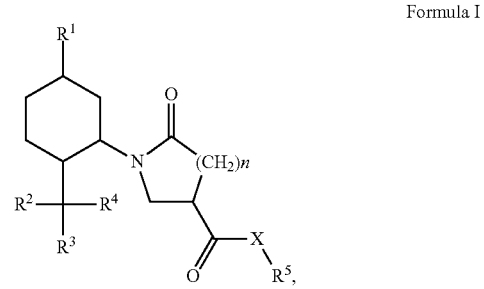

Formula I wherein n is an integer of 1 or 2;
$R^1, R^2, R^3$, and $R^4$ are each independently selected from the group consisting of hydrogen and methyl;
X is selected from the group consisting of oxygen and nitrogen; and
$R^5$ is hydrogen or a $C_1$-$C_7$ linear or branched acyclic hydrocarbon group, or $R^5$ together with X form a 3- to 8-membered heterocyclic hydrocarbon group, and their uses as cooling compounds.

15 Claims, No Drawings

DERIVATIVES OF 1-ALKYL-6-OXO-PIPERIDINE-3-CARBOXYLIC ACIDS AND 1-ALKYL-5-OXO-PYRROLIDINE-3-CARBOXYLIC ACIDS AND THEIR USES AS COOLING COMPOUNDS

FIELD OF THE INVENTION

The present invention relates to new chemical entities and the incorporation and use of the new chemical entities as cooling compounds.

BACKGROUND OF THE INVENTION

A large number of compounds are known to be useful in providing a cooling sensation in the mouth, in the nasal cavity and/or on the skin. The best known and most widely used of these is menthol, which in addition to olfaction causes a cooling response on cold receptors in the oral cavity, the nasal cavity and on the skin. Unfortunately, menthol also exhibits some undesirable properties, such as the strong mint smell, the bitter taste, and the relatively high volatility. These properties have limited the use of menthol in various applications and, therefore there remains a need for novel cooling compounds which provide strong and substantive cooling and refreshing attributes in the absence of negative aroma, negative taste, and negative cooling attributes.

SUMMARY OF THE INVENTION

The present invention provides novel cooling compounds, which exhibit surprisingly long-lasting cooling and refreshing effect and their use to provide cooling effect in the mouth and on the skin.

More specifically, the present invention is directed to novel derivatives of 1-alkyl-6-oxo-piperidine-3-carboxylic acids and 1-alkyl-5-oxo-pyrrolidine-3-carboxylic acids represented by Formula I set forth below:

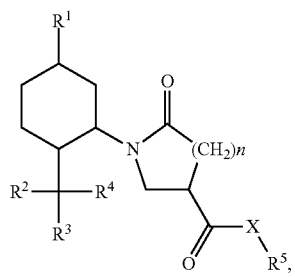

Formula I wherein n is an integer of 1 or 2;

$R^1$, $R^2$, $R^3$, and $R^4$ are each independently selected from the group consisting of hydrogen and methyl;

X is selected from the group consisting of oxygen and nitrogen; and $R^5$ is hydrogen or a $C_1$-$C_7$ linear or branched acyclic hydrocarbon group, or $R^5$ together with X form a 3- to 8-membered heterocyclic hydrocarbon group.

Another embodiment of the invention is directed to the derivatives of 1-alkyl-6-oxo-piperidine-3-carboxylic acids and 1-alkyl-5-oxo-pyrrolidine-3-carboxylic acids provided above, with the proviso that when X is oxygen, $R^5$ is selected from the group consisting of hydrogen and methyl.

Another embodiment of the invention is directed to a method of imparting cooling effect to foodstuff, a medicinal product, or a cosmetic product by incorporating an olfactory acceptable amount of the derivatives of 1-alkyl-6-oxo-piperidine-3-carboxylic acids and 1-alkyl-5-oxo-pyrrolidine-3-carboxylic acids provided above.

Another embodiment of the invention is directed to a composition comprising the derivatives of 1-alkyl-6-oxo-piperidine-3-carboxylic acids and 1-alkyl-5-oxo-pyrrolidine-3-carboxylic acids provided above and a material selected from the group consisting of foodstuff, a medicinal product, and a cosmetic product.

These and other embodiments of the present invention will be apparent by reading the following specification.

DETAILED DESCRIPTION OF THE INVENTION

It is known to those with the skill in the art that Formula I as defined above provides the following novel compounds:

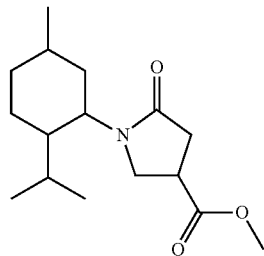

Structure I

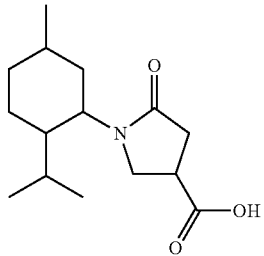

Structure II

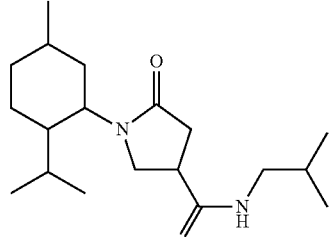

Structure III

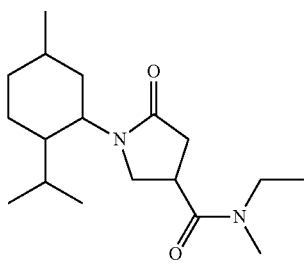

Structure IV

-continued

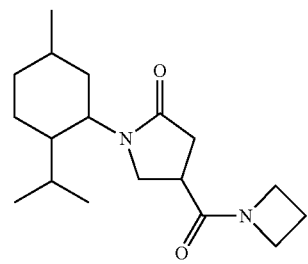
Structure V

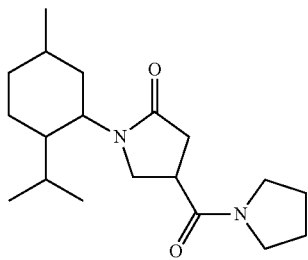
Structure VI

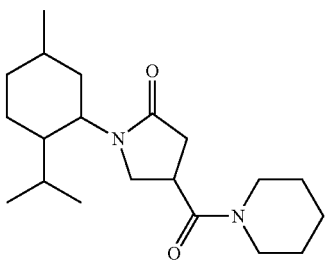
Structure VII

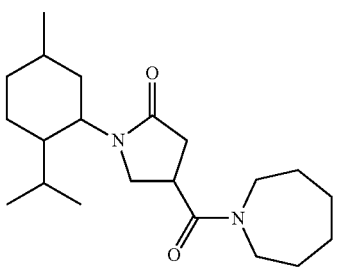
Structure VIII

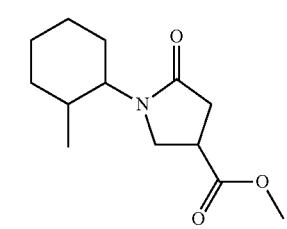
Structure IX

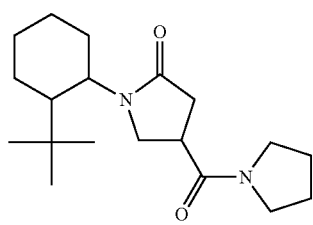
Structure X

-continued

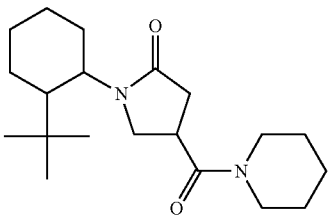
Structure XI

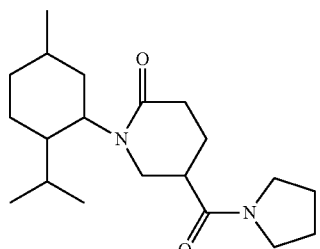
Structure XII

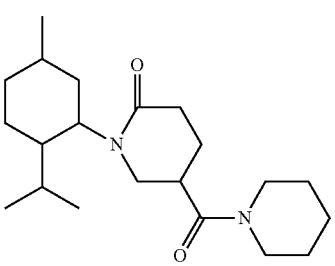
Structure XIII

Those with the skill in the art will recognize that:

Structure I represents 1-(2-isopropyl-5-methyl-cyclohexyl)-5-oxo-pyrrolidine-3-carboxylic acid methyl ester;

Structure II represents 1-(2-isopropyl-5-methyl-cyclohexyl)-5-oxo-pyrrolidine-3-carboxylic acid;

Structure III represents 1-(2-isopropyl-5-methyl-cyclohexyl)-5-oxo-pyrrolidine-3-carboxylic acid isobutyl-amide;

Structure IV represents 1-(2-isopropyl-5-methyl-cyclohexyl)-5-oxo-pyrrolidine-3-carboxylic acid ethyl-methyl-amide;

Structure V represents 4-(azetidine-1-carbonyl)-1-(2-isopropyl-5-methyl-cyclohexyl)-pyrrolidin-2-one;

Structure VI represents 1-(2-isopropyl-5-methyl-cyclohexyl)-4-(pyrrolidine-1-carbonyl)-pyrrolidin-2-one;

Structure VII represents 1-(2-isopropyl-5-methyl-cyclohexyl)-4-(piperidine-1-carbonyl)-pyrrolidin-2-one;

Structure VIII represents 4-(azepane-1-carbonyl)-1-(2-isopropyl-5-methyl-cyclohexyl)-pyrrolidin-2-one;

Structure IX represents 1-(2-methyl-cyclohexyl)-5-oxo-pyrrolidine-3-carboxylic acid methyl ester;

Structure X represents 1-(2-tert-butyl-cyclohexyl)-4-(pyrrolidine-1-carbonyl)-pyrrolidin-2-one;

Structure XI represents 1-(2-tert-butyl-cyclohexyl)-4-(piperidine-1-carbonyl)-pyrrolidin-2-one;

Structure XII represents 1-(2-isopropyl-5-methyl-cyclohexyl)-5-(pyrrolidine-1-carbonyl)-piperidin-2-one; and Structure XIII represents 1-(2-isopropyl-5-methyl-cyclohexyl)-5-(piperidine-1-carbonyl)-piperidin-2-one.

The compounds of the present invention may be prepared with corresponding cyclohexylamines via a reaction scheme illustrated as follows:

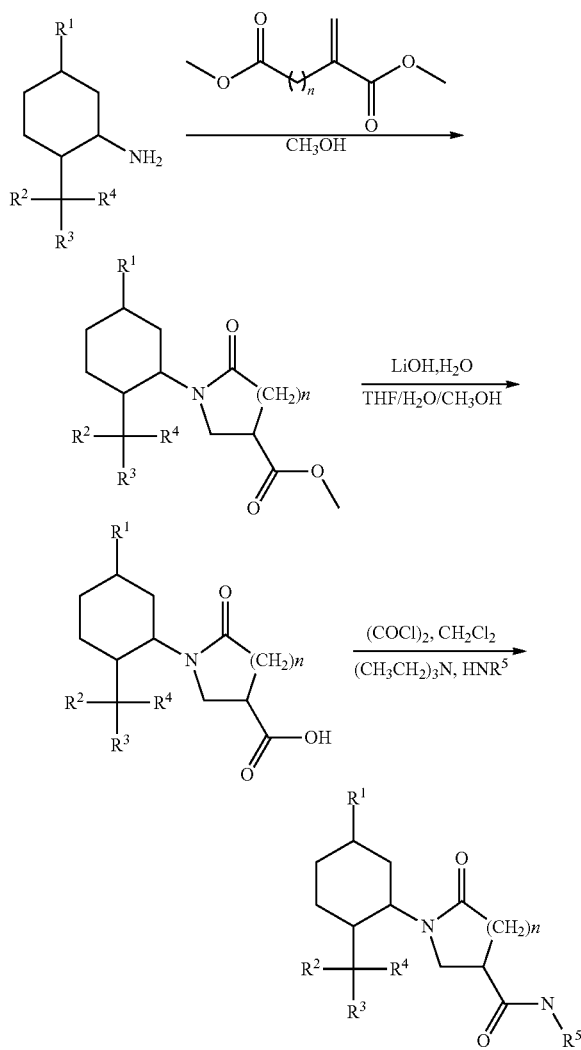

wherein n, $R^1$, $R^2$, $R^3$, $R^4$, and $R^5$ are as defined above; and THF represents tetrahydrofuran.

Those with skill in the art will recognize that some of the compounds of the present invention have a number of chiral centers, thereby providing numerous isomers of the claimed compounds. It is intended herein that the compounds described herein include isomeric mixtures of such compounds, as well as those isomers that may be separated using techniques known to those having skill in the art. Suitable techniques include chromatography such as high performance liquid chromatography, referred to as HPLC, and particularly silica gel chromatography and solid phase microextraction, referred to as SPME.

The compounds of the present invention are found to have unexpected long-lasting cooling and refreshing effect, which is shown to be advantageous for their use in providing cooling effect in the mouth and on the skin.

The present invention relates to a method of augmenting or imparting cooling effect to foodstuff such as but not limited to dairy products, ice confections, confectionery products, gums including chewing gums, candies, fondants, and beverages including but not limited to mineral water, alcoholic beverages, non-alcoholic beverages, and powdered beverages; medicinal products such as but not limited to mouth and throat lozenges, cough mixtures, decongestants, antacids, oral analgesics, topical preparations, and dental and oral hygiene products including but not limited to toothpastes, tooth gels, and mouthwashes; cosmetics such as but not limited to shaving balm, after-shave lotion, soaps, hair care products, shower gels, bath oils, skin care products, and lipstick products, perfumes, and colognes.

The compounds of the present invention can be used alone or in combination with other flavor ingredients including solvents, vehicles, stabilizers, thickeners, surface active agents, conditioners, and intensifiers. The nature and variety of these other ingredients are known to those with skill in the art.

The term "foodstuff" as used herein includes both solid and liquid ingestible materials for man or animals, which materials usually do, but need not, have nutritional value. Thus, foodstuffs include food products, such as, meat, vegetables, gravy, soups, convenience food, malt, mineral water, alcoholic beverages, non-alcoholic beverages, powdered beverages, dairy products, ice confection, confectionery products, gums including chewing gums, candies, cereals, snacks, fondants, seafood including fish, crustaceans, mollusks and the like, dog and cat foods, other veterinary products and the like.

The terms "flavor composition" and "flavor formulation" are understood to mean the same and refer to a formulation that is intended for providing a flavor character to foodstuff, medicinal products, and cosmetic products. The flavor composition of the present invention is a composition comprising a compound of the present invention.

As used herein, an olfactory effective amount is understood to mean the amount of the compound in a flavor or fragrance composition contributes to its particular olfactory characteristics, but the flavor, taste and aroma effect on the overall composition will be the sum of the effect of each flavor or fragrance ingredient. Thus the compounds of the present invention can be used to alter the characteristics of a flavor or fragrance composition, or by modifying the flavor, taste and aroma reaction contributed by another ingredient in the composition. The amount will vary depending on many factors including other ingredients, their relative amounts and the effect that is desired.

The usage level of the compounds of the present invention varies depending on the product in which the compounds are employed. Generally, the level of the derivatives of 1-alkyl-6-oxo-piperidine-3-carboxylic acids and 1-alkyl-5-oxo-pyrrolidine-3-carboxylic acids employed in a product is greater than about 1 part per billion by weight, preferably from about 0.1 to about 10,000 parts per million by weight, more preferably from about 50 to about 5000 parts per million by weight.

The following are provided as specific embodiments of the present invention. Other modifications of this invention will be readily apparent to those skilled in the art. Such modifications are understood to be within the scope of this invention. Reagents are all commercially available at Sigma-Aldrich, Co. unless otherwise noted. As used herein all percentages are weight percent unless otherwise noted, ppb is understood to be parts per billion, ppm is understood to be parts per million, L is understood to be liter, mL is understood to be milliliter, μL is understood to be microliter, g is understood to be gram, mol is understood to be mole, mmol is understood to be millimole, and N is understood be normal. IFF as used in the examples is understood to mean International Flavors & Fragrances Inc., New York, N.Y., USA.

EXAMPLE I

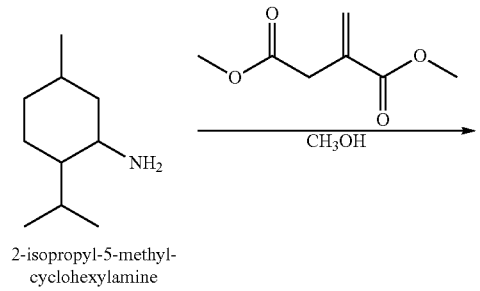

2-isopropyl-5-methyl-cyclohexylamine

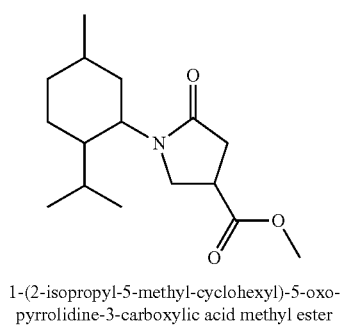

1-(2-isopropyl-5-methyl-cyclohexyl)-5-oxo-pyrrolidine-3-carboxylic acid methyl ester Preparation of 1-(2-Isopropyl-5-methyl-cyclohexyl)-5-oxo-pyrrolidine-3-carboxylic Acid Methyl Ester (Structure I): First, 2-isopropyl-5-methyl-cyclohexylamine was synthesized as previously described [Schopohl, et al., Synthesis 2003(17): 2689-2694] (40 g, 0.258 mol) and added dropwise to a solution of dimethyl itaconate ($CH_3O_2CCH_2C(=CH_2)CO_2CH_3$) (41 g, 0.258 mol) in methanol (50 mL) at room temperature. The reaction mixture was stirred for 12 hours at room temperature and the solvent was then removed in vacuo. The residue was dissolved in xylene (150 mL) and further stirred under reflux for 4 hours in the presence of a catalytic amount of p-toluenesulphonic acid (PTSA). The organic phase was washed twice with water (50 mL), the solvent was evaporated. Column chromatography with hexane:ethyl acetate (50:50) provided 1-(2-isopropyl-5-methyl-cyclohexyl)-5-oxo-pyrrolidine-3-carboxylic acid methyl ester (60 g).

$^1$H NMR (500 MHz, $CDCl_3$) δ: 0.79 ppm (d, 3H, J=6.81 Hz), 0.79-0.88 ppm (m, 1H), 0.90 ppm (d, 6H, J=6.55 Hz), 1.03-1.62 ppm (m, 5H), 1.64-1.74 ppm (m, 3H), 2.68 ppm (d, 2H, J=9.06 Hz), 3.19 ppm (pentet, 1H, J=8.30 Hz), 3.41 ppm (t, 1H, J=8.93 Hz), 3.52 ppm (t, 1H, J=8.41 Hz), 3.74 ppm (s, 3H), 3.96 ppm (br. s, 1H).

1-(2-Isopropyl-5-methyl-cyclohexyl)-5-oxo-pyrrolidine-3-carboxylic acid methyl ester (10 ppm in water) was described as having a mild cooling effect.

EXAMPLE II

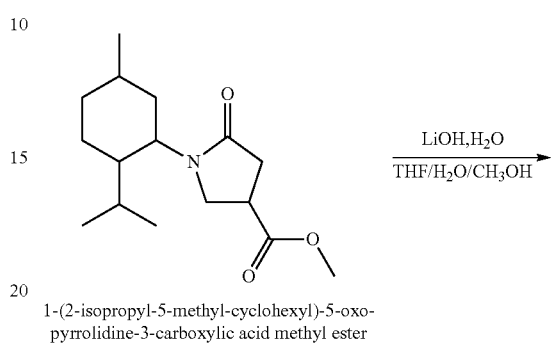

1-(2-isopropyl-5-methyl-cyclohexyl)-5-oxo-pyrrolidine-3-carboxylic acid methyl ester

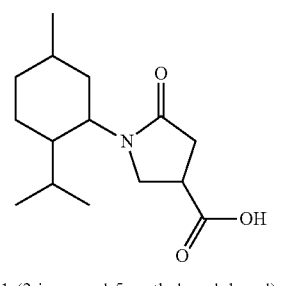

1-(2-isopropyl-5-methyl-cyclohexyl)-5-oxo-pyrrolidine-3-carboxylic acid

Preparation of 1-(2-Isopropyl-5-methyl-cyclohexyl)-5-oxo-pyrrolidine-3-carboxylic Acid (Structure II): Lithium hydroxide, monohydrate (LiOH, $H_2O$) (13.22 g, 0.315 mol) was added to a solution of 1-(2-isopropyl-5-methyl-cyclohexyl)-5-oxo-pyrrolidine-3-carboxylic acid methyl ester (obtained as in EXAMPLE I, 59 g, 0.21 mol,) in a mixture of tetrahydrofuran (THF:$H_2O$:$CH_3OH$) (1:1:1) (300 mL) at room temperature and was stirred for 1-2 hours. THF and $CH_3OH$ were then removed via evaporation. HCl was added and the reaction mixture was extracted three times with ethyl acetate. The organic fractions were combined, washed with brine, dried, and concentrated to provide 1-(2-isopropyl-5-methyl-cyclohexyl)-5-oxo-pyrrolidine-3-carboxylic acid (50 g), which was further evaporated with benzene twice to remove traces of water.

$^1$H NMR (500 MHz, $CDCl_3$) δ: 0.76 ppm (d, 3H, J=6.73 Hz), 0.80-0.84 ppm (m, 1H), 0.89 ppm (d, 6H, J=7.44 Hz, of d, J=7.26 Hz), 0.94-1.12 ppm (m, 2H), 1.27 ppm (m, 1H), 1.41-1.74 ppm (m, 5H), 2.69-2.84 ppm (m, 2H), 3.22 ppm (pentet, 1H, J=6.27 Hz), 3.43-3.46 ppm (m, 1H), 3.57 ppm (d, 1H, J=8.99 Hz), 3.98 ppm (br. s, 1H).

1-(2-Isopropyl-5-methyl-cyclohexyl)-5-oxo-pyrrolidine-3-carboxylic acid (10 ppm in water) was described as having some cooling effect developed in the back of throat.

EXAMPLE III

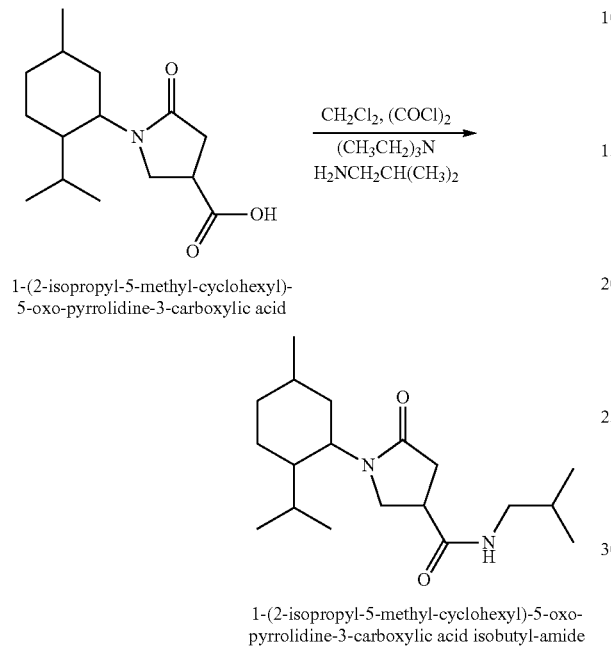

1-(2-isopropyl-5-methyl-cyclohexyl)-5-oxo-pyrrolidine-3-carboxylic acid 1-(2-isopropyl-5-methyl-cyclohexyl)-5-oxo-pyrrolidine-3-carboxylic acid isobutyl-amide Preparation of 1-(2-Isopropyl-5-methyl-cyclohexyl)-5-oxo-pyrrolidine-3-carboxylic Acid Isobutyl-amide (Structure III): Oxalyl chloride ((COCl)$_2$) (350 mg, 2.8 mmol, 240 mL) and dimethylformamide (DMF; (CH$_3$)$_2$NC(O)H catalytic) (20 µL) were carefully added to 1-(2-isopropyl-5-methyl-cyclohexyl)-5-oxo-pyrrolidine-3-carboxylic acid (obtained as in EXAMPLE II, 500 mg, 1.87 mmol) suspended in anhydrous dichloromethane (CH$_2$Cl$_2$) (10 mL). The reaction mixture slowly turned into a homogeneous solution over about 3 hours, which was then concentrated in vacuo to remove (COCl)$_2$. The resulted raw oil was dissolved in anhydrous CH$_2$Cl$_2$ and subsequently added dropwise to a mixture of N,N-diisopropylethylamine (DIEA; (CH$_3$CH$_2$)$_3$N) (290 mg, 2.24 mmol) and isobutylamine (H$_2$NCH$_2$CH(CH$_3$)$_2$) (160 mg, 2.24 mmol) at 0° C. with stirring. The reaction mixture was allowed to warm to room temperature and stirred for 3 hours. The reaction mixture was poured into HCl (1 N) and extracted with CH$_2$Cl$_2$. The organic phases were collected, washed with brine, dried, and evaporated. Column chromatography with ethyl:acetate (50:50) provided 1-(2-isopropyl-5-methyl-cyclohexyl)-5-oxo-pyrrolidine-3-carboxylic acid isobutyl-amide (390 mg, 1.2 mmol).

$^1$H NMR (500 MHz, CDCl$_3$) δ: 0.78 ppm (d, 3H, J=6.84 Hz), 0.80-0.87 ppm (m, 1H), 0.89 ppm (d, 6H, J=6.64 Hz), 0.92 ppm (d, 6H, J=6.69 Hz), 1.05-1.38 ppm (m, 2H), 1.42-1.54 ppm (m, 2H), 1.60-1.82 ppm (m, 5H), 2.55-2.61 ppm (2d, 1H, J=9.54 and 9.48 Hz), 2.70-2.76 ppm (2d, 1H, J=8.41 and 8.40 Hz), 2.97 ppm (pentet, 1H, J=8.46 Hz), 3.12 ppm (t, 2H, J=6.41 Hz), 3.48 ppm (d, 2H, J=7.74 Hz), 3.98 ppm (br. s, 1H), 5.50 ppm (br. s, 1H).

1-(2-Isopropyl-5-methyl-cyclohexyl)-5-oxo-pyrrolidine-3-carboxylic acid isobutyl-amide (10 ppm in water) was described as having a mild cooling effect.

EXAMPLE IV

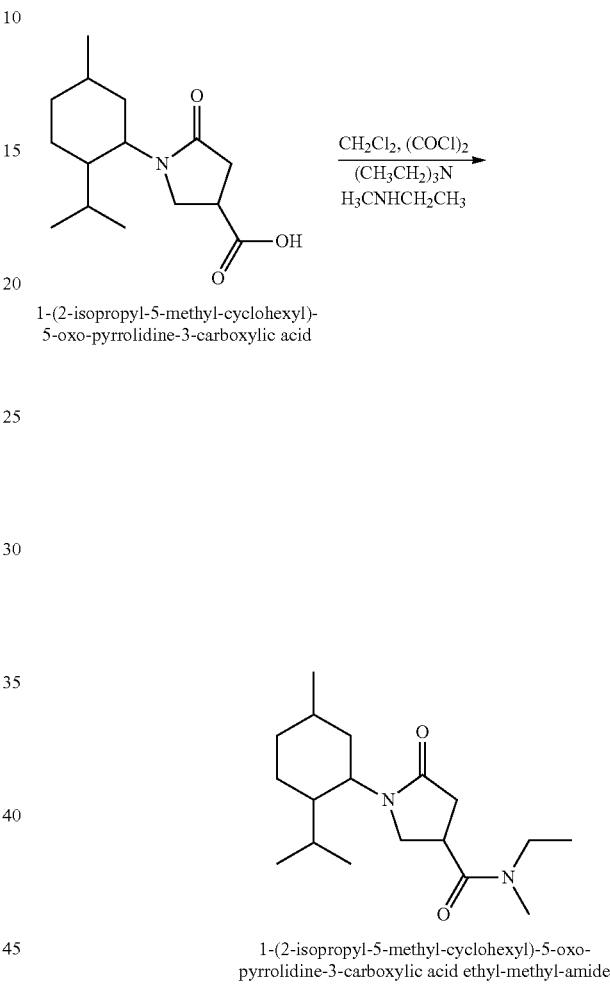

1-(2-isopropyl-5-methyl-cyclohexyl)-5-oxo-pyrrolidine-3-carboxylic acid 1-(2-isopropyl-5-methyl-cyclohexyl)-5-oxo-pyrrolidine-3-carboxylic acid ethyl-methyl-amide Preparation of 1-(2-Isopropyl-5-methyl-cyclohexyl)-5-oxo-pyrrolidine-3-carboxylic Acid Ethyl-methyl-amide (Structure IV): 1-(2-Isopropyl-5-methyl-cyclohexyl)-5-oxo-pyrrolidine-3-carboxylic acid ethyl-methyl-amide was similarly prepared as described in Examples I, II, and III. 1-(2-Isopropyl-5-methyl-cyclohexyl)-5-oxo-pyrrolidine-3-carboxylic acid (obtained as in EXAMPLE II, 500 mg, 1.64 mmol) was used to provide 1-(2-isopropyl-5-methyl-cyclohexyl)-5-oxo-pyrrolidine-3-carboxylic acid ethyl-methyl-amide (350 mg, 1.15 mmol).

$^1$H NMR (500 MHz, CDCl$_3$) δ: 0.79 ppm (d, 3H, J=6.78 Hz), 0.81-0.84 ppm (m, 1H), 0.89 ppm (2d, 6H, J=6.78 and 6.42 Hz), 1.11 ppm (t, 3H, J=6.78 and 6.42 Hz), 1.24-1.75 ppm (m, 8H), 2.50-2.70 ppm (m, 2H), 2.62 ppm (s, ~50% of 3H), 2.63 ppm (s, ~50% of 3H), 3.23-3.34 ppm (m, 3H), 3.34-3.49 ppm (m, 1H), 3.72 (br. s, 1H), 3.95 ppm (br. s, 1H).

1-(2-Isopropyl-5-methyl-cyclohexyl)-5-oxo-pyrrolidine-3-carboxylic acid ethyl-methyl-amide (10 ppm in water) was described as having a mild cooling effect.

EXAMPLE V

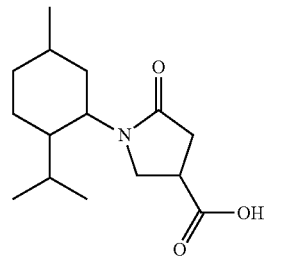

1-(2-isopropyl-5-methyl-cyclohexyl)-
5-oxo-pyrrolidine-3-carboxylic acid $\xrightarrow[\text{azetidine}]{\text{CH}_2\text{Cl}_2,\ (\text{COCl})_2 \atop (\text{CH}_3\text{CH}_2)_3\text{N}}$

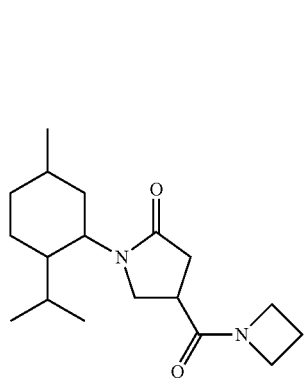

4-(azetidine-1-carbonyl)-1-(2-isopropyl-
5-methyl-cyclohexyl)-pyrrolidin-2-one

Preparation of 4-(Azetidine-1-carbonyl)-1-(2-isopropyl-5-methyl-cyclohexyl)-pyrrolidin-2-one (Structure V): 4-(Azetidine-1-carbonyl)-1-(2-isopropyl-5-methyl-cyclohexyl)-pyrrolidin-2-one was similarly prepared as described in Examples I, II, and III. 1-(2-Isopropyl-5-methyl-cyclohexyl)-5-oxo-pyrrolidine-3-carboxylic acid (obtained as in EXAMPLE II, 1 g, 3.8 mmol) was used to provide 4-(azetidine-1-carbonyl)-1-(2-isopropyl-5-methyl-cyclohexyl)-pyrrolidin-2-one (800 mg, 2.66 mmol).

$^1$H NMR (500 MHz, CDCl$_3$) δ: 0.78 ppm (m, 3H), 0.80-0.84 ppm (m, 1H), 0.89 ppm (d, 6H, J=6.64 Hz), 1.05-1.18 ppm (m, 2H), 1.19-1.35 ppm (m, 1H), 1.45-1.65 ppm (m, 2H), 1.66-1.75 ppm (m, 3H), 2.33 ppm (pentet, 2H, J=7.67 Hz), 2.50-2.80 ppm (m, 2H), 2.98-3.08 ppm (m, 1H), 3.20-3.61 ppm (m, 2H), 3.95 ppm (m, 1H), 4.05 ppm (t, 2H, J=7.70 Hz), 4.17-4.22 ppm (m, 2H).

4-(Azetidine-1-carbonyl)-1-(2-isopropyl-5-methyl-cyclohexyl)-pyrrolidin-2-one (40 ppm in water) was described as having mild cooling, earthy, off-flavor, not bitter, napthalene, herbaceous, slight tingle effect on the tip of tongue, and garden hose, carrot, astringent, and waxy effect.

EXAMPLE VI

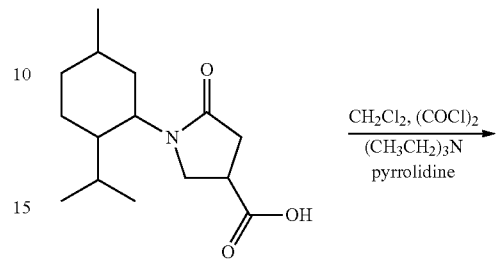

1-(2-isopropyl-5-methyl-cyclohexyl)-
5-oxo-pyrrolidine-3-carboxylic acid $\xrightarrow[\text{pyrrolidine}]{\text{CH}_2\text{Cl}_2,\ (\text{COCl})_2 \atop (\text{CH}_3\text{CH}_2)_3\text{N}}$

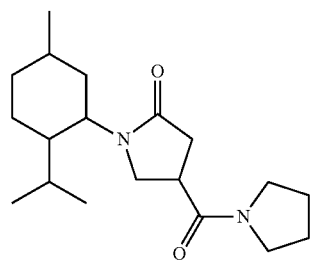

1-(2-isopropyl-5-methyl-cyclohexyl)-4-
(pyrrolidine-1-carbonyl)-pyrrolidin-2-one Preparation of 1-(2-Isopropyl-5-methyl-cyclohexyl)-4-(pyrrolidine-1-carbonyl)-pyrrolidin-2-one (Structure VI): 1-(2-Isopropyl-5-methyl-cyclohexyl)-4-(pyrrolidine-1-carbonyl)-pyrrolidin-2-one was similarly prepared as described in Examples I, II, and III. 1-(2-Isopropyl-5-methyl-cyclohexyl)-5-oxo-pyrrolidine-3-carboxylic acid (obtained as in EXAMPLE II, 10 g, 37.5 mmol) was used to provide 4-(azetidine-1-carbonyl)-1-(2-isopropyl-5-methyl-cyclohexyl)-pyrrolidin-2-one (10.2 mg, 32 mmol).

$^1$H NMR (500 MHz, CDCl$_3$) δ: 0.78 ppm (d, 3H, J=6.84 Hz), 0.80-0.88 ppm (m, 1H), 0.90 ppm (d, 3H, J=6.44 Hz), 0.90 ppm (d, 3H, J=6.93 Hz), 1.06-1.14 ppm (m, 2H), 1.20-1.31 ppm (m, 1H), 1.61-1.77 ppm (m, 5H), 1.87-1.92 ppm (m, 2H), 1.98-2.02 ppm (m, 2H), 2.60 ppm (2d, 1H, J=9.66 and 9.57 Hz), 2.74 ppm (2d, 1H, J=9.12 and 8.79 Hz), 3.25 ppm (pentet, 1H, J=8.70 Hz), 3.46 ppm (m, 5H), 3.56 ppm (m, 1H), 3.95-4.02 ppm (m, 1H).

1-(2-Isopropyl-5-methyl-cyclohexyl)-4-(pyrrolidine-1-carbonyl)-pyrrolidin-2-one was described as, at 10 ppm in water, having mild cooling effect with slight bitterness, the cooling effect built up over the time; and at 50 ppm in water, having cooling effect with bitterness, a menthol-like burning taste, and a nice built-up cooling taste.

EXAMPLE VII

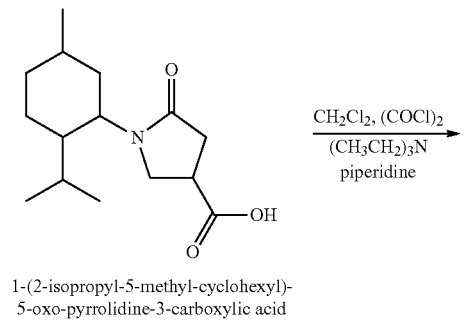

1-(2-isopropyl-5-methyl-cyclohexyl)-
5-oxo-pyrrolidine-3-carboxylic acid

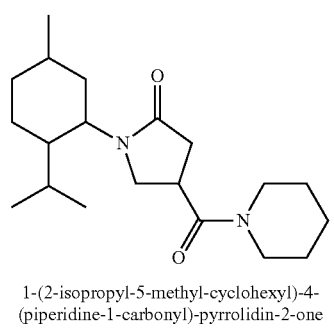

1-(2-isopropyl-5-methyl-cyclohexyl)-4-
(piperidine-1-carbonyl)-pyrrolidin-2-one

Preparation of 1-(2-Isopropyl-5-methyl-cyclohexyl)-4-(piperidine-1-carbonyl)-pyrrolidin-2-one (Structure VII): $(COCl)_2$ (10 g, 79 mmol, 6.9 mL) and DMF (50 µL) were carefully added to 1-(2-isopropyl-5-methyl-cyclohexyl)-5-oxo-pyrrolidine-3-carboxylic acid (obtained as in EXAMPLE II, 10 g, 37.4 mmol) suspended in anhydrous $CH_2Cl_2$ (150 mL). The reaction mixture slowly turned into a homogeneous solution over about 3 hours, which was then concentrated in vacuo and dissolved in anhydrous $CH_2Cl_2$. The reaction mixture was subsequently added dropwise to a mixture of DIEA (9.7 g, 74.8 mmol) and piperidine (3.99 g, 56 mmol) at 0° C. with stirring. The reaction mixture was allowed to warm to room temperature and stirred for 3 hours. The reaction mixture was poured into HCl (1 N) and extracted with $CH_2Cl_2$. The organic phases were collected, washed with brine, dried, and evaporated. Column chromatography with dichloromethane:methanol (95:5) provided 1-(2-isopropyl-5-methyl-cyclohexyl)-4-(piperidine-1-carbonyl)-pyrrolidin-2-one (10.8 g).

$^1$H NMR (500 MHz, CDCl$_3$) δ: 0.78 ppm (2d, 3H, J=6.86 and 6.86 Hz), 0.81-0.85 ppm (m, 1H), 0.88-0.91 ppm (2d, 6H), 1.07-1.23 ppm (m, 2H), 1.24-1.38 ppm (m, 1H), 1.50-1.63 ppm (m, 6H), 1.64-1.74 ppm (m, 5H), 2.54-2.77 ppm (m, 2H), 3.23-3.75 ppm (m, 7H), 3.96 ppm (m, 1H).

1-(2-Isopropyl-5-methyl-cyclohexyl)-4-(piperidine-1-carbonyl)-pyrrolidin-2-one (40 ppm in water) was described as having slight upfront bitterness, herbaceous flavor, and built-up cooling effect.

EXAMPLE VIII

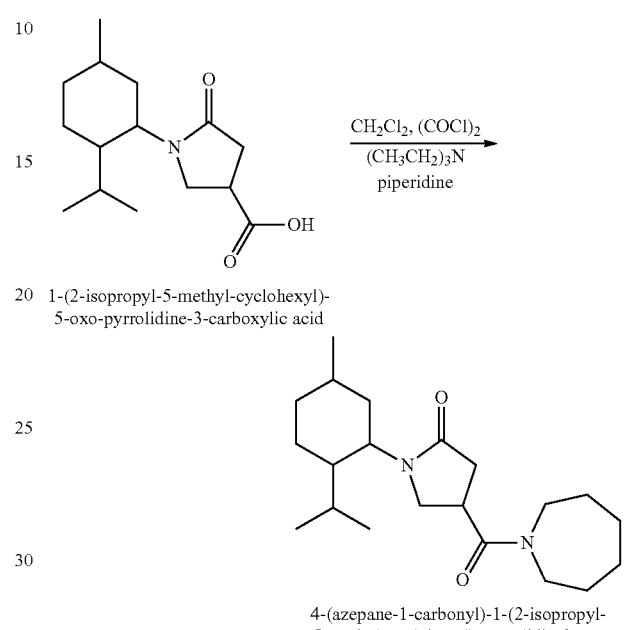

1-(2-isopropyl-5-methyl-cyclohexyl)-
5-oxo-pyrrolidine-3-carboxylic acid 4-(azepane-1-carbonyl)-1-(2-isopropyl-
5-methyl-cyclohexyl)-pyrrolidin-2-one Preparation of 4-(Azepane-1-carbonyl)-1-(2-isopropyl-5-methyl-cyclohexyl)-pyrrolidin-2-one (Structure VIII): 1-(2-Isopropyl-5-methyl-cyclohexyl)-4-(pyrrolidine-1-carbonyl)-pyrrolidin-2-one was similarly prepared as described in Examples I, II, and III. 1-(2-Isopropyl-5-methyl-cyclohexyl)-5-oxo-pyrrolidine-3-carboxylic acid (obtained as in EXAMPLE II, 5 g, 18.7 mmol) was used to provide 4-(azepane-1-carbonyl)-1-(2-isopropyl-5-methyl-cyclohexyl)-pyrrolidin-2-one (5.2 g, 15 mmol).

$^1$H NMR (500 MHz, CDCl$_3$) δ: 0.77 ppm (2d, 3H, J=6.78 and 6.78 Hz), 0.79-0.87 ppm (m, 1H), 0.88-0.90 ppm (m, 6H), 1.02-1.18 ppm (m, 2H), 1.19-1.34 ppm (m, 1H), 1.45-1.63 ppm (m, 7H), 1.64-1.79 ppm (m, 6H), 2.57-2.82 ppm (m, 2H), 3.16-3.74 ppm (m, 7H), 3.95 ppm (m, 1H).

4-(Azepane-1-carbonyl)-1-(2-isopropyl-5-methyl-cyclohexyl)-pyrrolidin-2-one (40 ppm in water) was described as having bitterness and cooling effect and both built up.

EXAMPLE IX

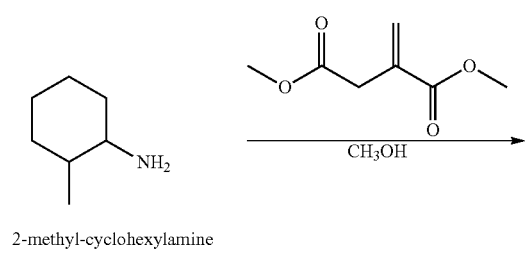

2-methyl-cyclohexylamine

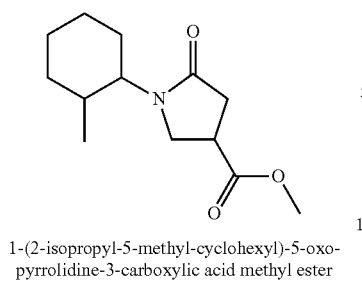

1-(2-isopropyl-5-methyl-cyclohexyl)-5-oxo-pyrrolidine-3-carboxylic acid methyl ester

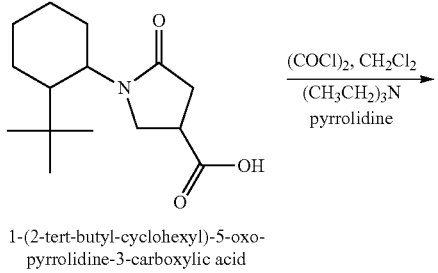

1-(2-tert-butyl-cyclohexyl)-5-oxo-pyrrolidine-3-carboxylic acid

Preparation of 1-(2-Methyl-cyclohexyl)-5-oxo-pyrrolidine-3-carboxylic Acid Methyl Ester (Structure IX): 1-(2-Methyl-cyclohexyl)-5-oxo-pyrrolidine-3-carboxylic acid methyl ester was prepared with 2-methyl-cyclohexylamine in the manner described above for 1-(2-isopropyl-5-methyl-cyclohexyl)-5-oxo-pyrrolidine-3-carboxylic acid methyl ester of Example I. 2-Methyl-cyclohexylamine (7.4 g, 47.7 mmol) was used to provide 1-(2-methyl-cyclohexyl)-5-oxo-pyrrolidine-3-carboxylic acid methyl ester (10.7 g, 38.2 mmol).

$^1$H NMR (500 MHz, CDCl$_3$) δ: 0.81-0.84 ppm (2d, ~58% of 3H, J=6.48 and 6.47 Hz), 0.92-0.97 ppm (m, ~42% of 3H), 1.08-1.82 ppm (m, 9H), 2.16-2.30 ppm (m, 1H), 2.61-2.76 ppm (m, 2H), 3.17-3.25 ppm (m, 1H), 3.46-3.71 ppm (m, 2H), 3.74 ppm (2s, 3H).

1-(2-Methyl-cyclohexyl)-5-oxo-pyrrolidine-3-carboxylic acid methyl ester (40 ppm in water) was described as having slight upfront bitterness for ~20-30 seconds and mild cooling effect that slightly built up in a few minutes.

EXAMPLE X

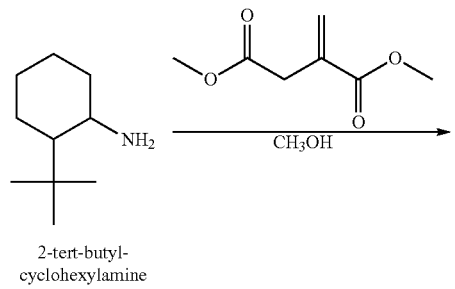

2-tert-butyl-cyclohexylamine

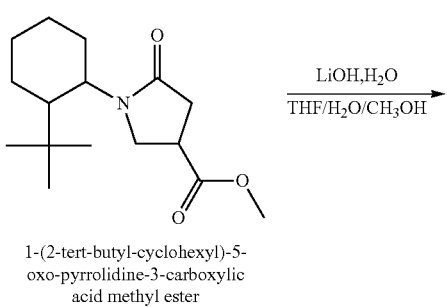

1-(2-tert-butyl-cyclohexyl)-5-oxo-pyrrolidine-3-carboxylic acid methyl ester

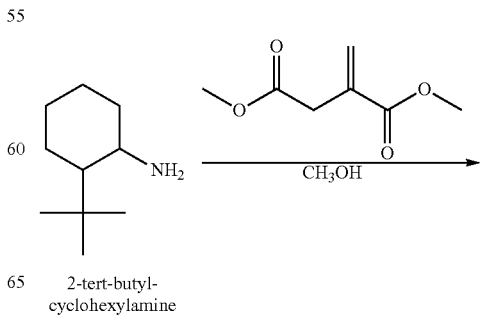

1-(2-tert-butyl-cyclohexyl)-4-(pyrrolidine-1-carbonyl)-pyrrolidin-2-one

Preparation of 1-(2-tert-Butyl-cyclohexyl)-4-(pyrrolidine-1-carbonyl)-pyrrolidin-2-one (Structure X): 1-(2-tert-Butyl-cyclohexyl)-4-(pyrrolidine-1-carbonyl)-pyrrolidin-2-one was similarly prepared as described in Examples I, II, and VI. 2-tert-Butylcyclohexanone (commercially available at Alfa Aesar GmbH & Co. KG) was used to obtain 1-(2-tert-butyl-cyclohexyl)-5-oxo-pyrrolidine-3-carboxylic acid (1 g, 3.74 mmol), which was subsequently used to provide 1-(2-tert-butyl-cyclohexyl)-4-(pyrrolidine-1-carbonyl)-pyrrolidin-2-one (1.1 g, 3.2 mmol).

$^1$H NMR (500 MHz, CDCl$_3$) δ: 0.93 ppm (2s, 9H), 0.99-2.02 ppm (m, 13H), 2.50-2.73, (m, 2H), 3.10-3.30 ppm (m, 1H), 3.43-3.53 ppm (m, 4H), 3.53-4.70 ppm (m, 3H).

1-(2-tert-Butyl-cyclohexyl)-4-(pyrrolidine-1-carbonyl)-pyrrolidin-2-one (40 ppm in water) was described as having upfront bitterness, quinine, drying, greasy, and burning effect.

EXAMPLE XI

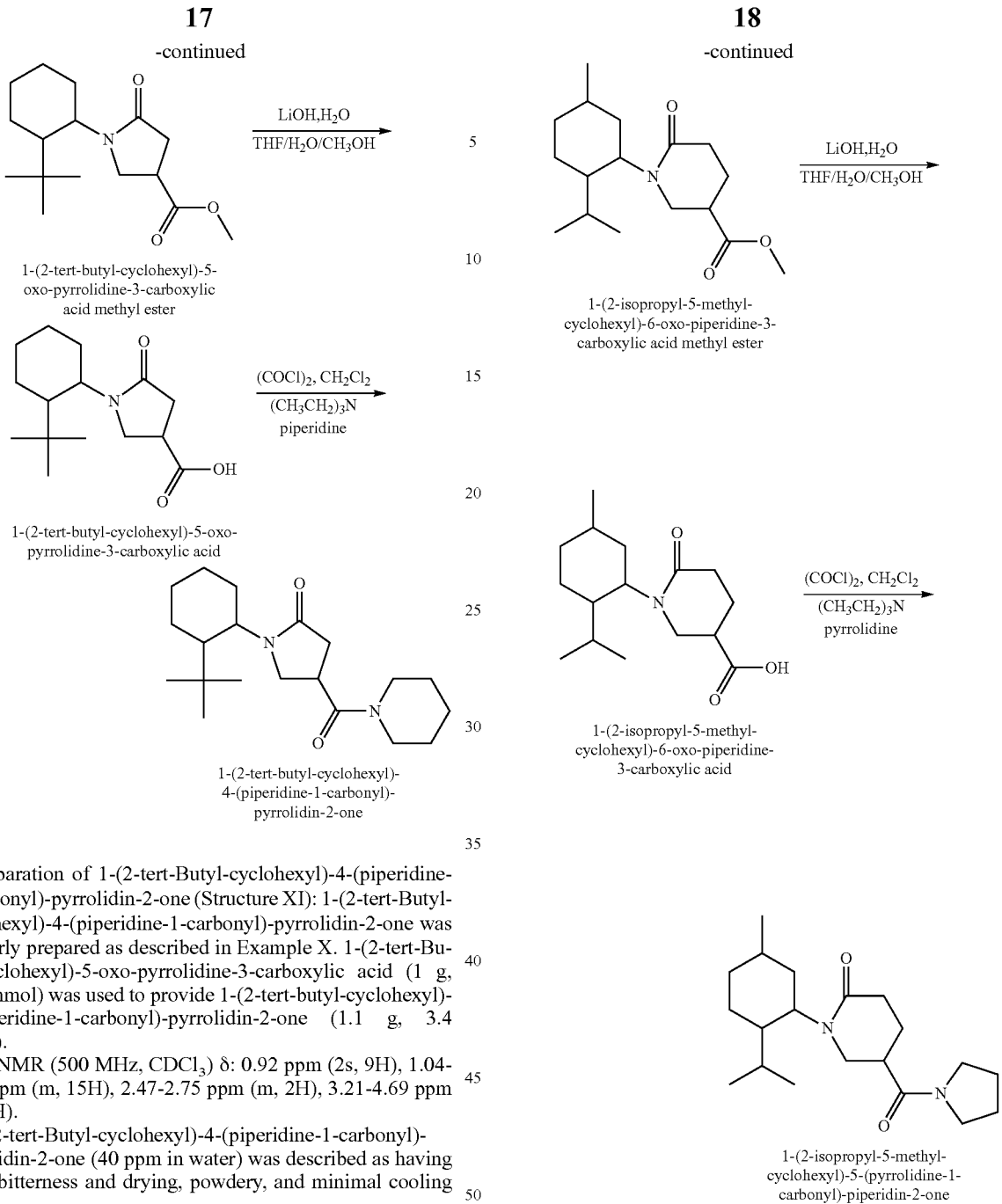

Preparation of 1-(2-tert-Butyl-cyclohexyl)-4-(piperidine-1-carbonyl)-pyrrolidin-2-one (Structure XI): 1-(2-tert-Butyl-cyclohexyl)-4-(piperidine-1-carbonyl)-pyrrolidin-2-one was similarly prepared as described in Example X. 1-(2-tert-Butyl-cyclohexyl)-5-oxo-pyrrolidine-3-carboxylic acid (1 g, 3.74 mmol) was used to provide 1-(2-tert-butyl-cyclohexyl)-4-(piperidine-1-carbonyl)-pyrrolidin-2-one (1.1 g, 3.4 mmol).

$^1$H NMR (500 MHz, CDCl$_3$) δ: 0.92 ppm (2s, 9H), 1.04-2.08 ppm (m, 15H), 2.47-2.75 ppm (m, 2H), 3.21-4.69 ppm (m, 8H).

1-(2-tert-Butyl-cyclohexyl)-4-(piperidine-1-carbonyl)-pyrrolidin-2-one (40 ppm in water) was described as having some bitterness and drying, powdery, and minimal cooling effect.

EXAMPLE XII

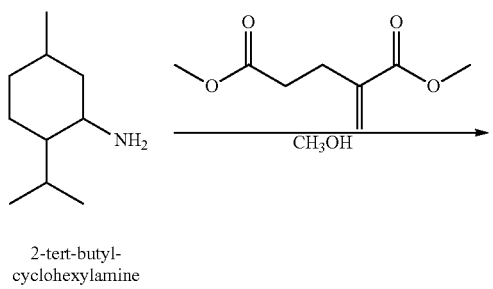

Preparation of 1-(2-Isopropyl-5-methyl-cyclohexyl)-5-(pyrrolidine-1-carbonyl)-piperidin-2-one (Structure XII): 1-(2-Isopropyl-5-methyl-cyclohexyl)-5-(pyrrolidine-1-carbonyl)-piperidin-2-one was similarly prepared as described in Examples I, II, and VI. 1-(2-Isopropyl-5-methyl-cyclohexyl)-6-oxo-piperidine-3-carboxylic acid (3 g, 10.67 mmol) was used to provide 1-(2-isopropyl-5-methyl-cyclohexyl)-5-(pyrrolidine-1-carbonyl)-piperidin-2-one (2.8 g, 8.5 mmol).

$^1$H NMR (500 MHz, CDCl$_3$) δ: 0.76-0.80 ppm (d, 3H, J=6.77 Hz, of d, J=5.20 Hz), 0.80-0.84 ppm (m, 1H), 0.87-0.91 ppm (m, 6H), 1.04-1.19 ppm (m, 2H), 1.25-1.36 ppm (m, 1H), 1.51-1.60 ppm (m, 2H), 1.64-1.73 ppm (m, 3H), 1.86-1.94 ppm (m, 2H), 1.94-2.04 ppm (m, 4H), 2.39-2.47, (m, 1H), 2.55-2.75 ppm (m, 2H), 3.13-3.54 ppm (m, 6H), 4.52-4.59 ppm (m, 1H).

1-(2-Isopropyl-5-methyl-cyclohexyl)-5-(pyrrolidine-1-carbonyl)-piperidin-2-one (40 ppm in water) was described as having slight cooling, and bitter and drying effect.

EXAMPLE XIII

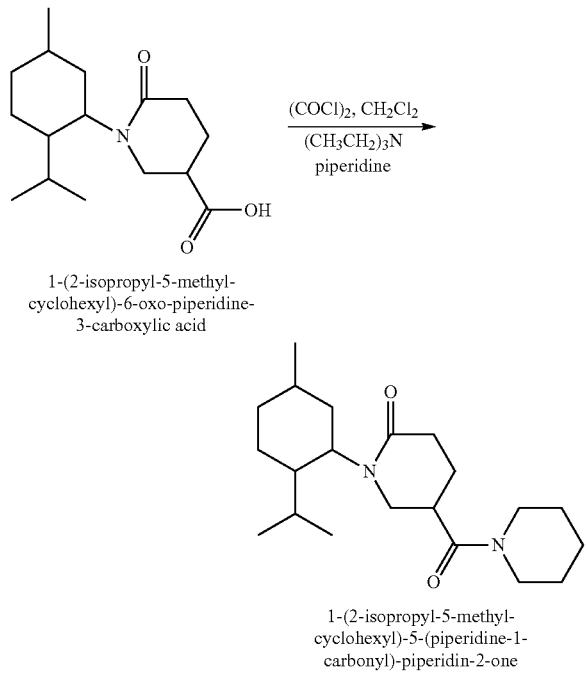

1-(2-isopropyl-5-methyl-cyclohexyl)-6-oxo-piperidine-3-carboxylic acid 1-(2-isopropyl-5-methyl-cyclohexyl)-5-(piperidine-1-carbonyl)-piperidin-2-one Preparation of 1-(2-Isopropyl-5-methyl-cyclohexyl)-5-(piperidine-1-carbonyl)-piperidin-2-one (Structure XIII): 1-(2-Isopropyl-5-methyl-cyclohexyl)-5-(piperidine-1-carbonyl)-piperidin-2-one was similarly prepared as described in Example XII. 1-(2-Isopropyl-5-methyl-cyclohexyl)-6-oxo-piperidine-3-carboxylic acid (3 g, 10.67 mmol) was used to provide 1-(2-isopropyl-5-methyl-cyclohexyl)-5-(piperidine-1-carbonyl)-piperidin-2-one (2.9 g, 8.5 mmol).

$^1$H NMR (500 MHz, CDCl$_3$) δ: 0.77-0.80 ppm (d, 3H, J=6.84 Hz, of d, J=3.22 Hz), 0.80-1.35 ppm (m, 4H), 0.88-0.91 ppm (m, 6H), 1.51-1.73 ppm (m, 11H), 1.92-1.98 ppm (m, 2H), 2.38-2.48 ppm (m, 1H), 2.53-2.62 ppm (m, 1H), 2.77-2.89 ppm (m, 1H), 3.11-3.65 ppm (m, 6H), 4.51-4.59 ppm (m, 1H).

1-(2-Isopropyl-5-methyl-cyclohexyl)-5-(piperidine-1-carbonyl)-piperidin-2-one (40 ppm in water) was described as having a grapefruit-like bitterness, and very mild cooling and drying effect.

EXAMPLE XIV

Preparation of a Gum

First, the following gum base formulation was prepared:

| Ingredients | Parts by Percentage (%) | Parts by Weight |
|---|---|---|
| Gum Base, Hades-T[1] | 29.35 | 205.45 |
| Maltitol Syrup | 3.00 | 21 |
| Sorbitol Powder | 48.30 | 338.1 |
| Mannitol Powder | 8.00 | 56 |
| Glycerin | 9.00 | 63 |
| Sucralose | 0.20 | 1.4 |
| Acesulfame K | 0.15 | 1.05 |
| Orange Flavor[2] | 1.00 | 7 |
| Total | 99.00 | 693 |

[1]Commercially available from Cafosa Gum, Barcelona, Spain;
[2]Commercially available from IFF.

The above formulation was prepared in a Sigma mixer. The resultant chewing gum blend was manufactured into strips of 1 inch in width and 0.1 inches in thickness. The strips were subsequently cut into a length of 3 inches each. A control gum as above exhibited orange flavor with no cooling effect. A test gum was further prepared by adding 1-(2-isopropyl-5-methyl-cyclohexyl)-4-(pyrrolidine-1-carbonyl)-pyrrolidin-2-one (Structure VI, 800 ppm) or 1-(2-isopropyl-5-methyl-cyclohexyl)-4-(piperidine-1-carbonyl)-pyrrolidin-2-one (Structure VII, 1200 ppm). The resulting test gums had a taste profile substantially identical to that of the control gum; however the test gum further exhibited pleasant cooling effect as described below:

EXAMPLE XIV (Continued)

| Group | Profile |
|---|---|
| Control Gum | Exhibited orange flavor without cooling. |
| Structure VII-containing Gum (1200 ppm) | At 0-1 minute: cooling onset, throat and slight tongue irritation, mild to medium bitterness, slight cooling in mouth and tongue; At 1-3 minutes: cooling and irritation delocalized with some concentration in the back of throat, cooling started to build up; At 3-5 minutes: full mouth cooling, throughout mouth but not overpowering, intense but more like black pepper burn, cooling built up and became stronger with strong cold sensation in mouth and throat; At 5-10 minutes: strong cooling in mouth, concentrated in the front (such as lips), sides, and roof with peppery feeling; At 10-20 minutes: cooling peaked, consistent without any decrease, strong in mouth and throat; At 20-30 minutes: strong cooling in mouth and throat, particularly in the back of mouth and throat as well as the back sides of tongue; |

| Group | Profile |
|---|---|
| Structure VI-containing Gum (800 ppm) | After 45 minutes: strong cooling persisted and radiated to the rear of throat.<br>At 0-1 minute: cooling began to build, localized on the tip of tongue;<br>At 1-3 minutes: cooling delocalized on the tongue;<br>At 3-5 minutes: mild cooling located on the tongue;<br>At 5-10 minutes: moderate cooling on the tongue and the roof of mouth;<br>At 10-20 minutes: cooling in the center of tongue and on the roof of mouth;<br>At 20-30 minutes: clean sensation with a little bitterness. |

EXAMPLE XV

Preparation of a Hard Candy

First, the following formulation was prepared:

| Ingredients | Parts by Weight (g) |
|---|---|
| Sucrose | 336 |
| Corn Syrup 42 DE | 162 |
| Water | 102 |

The above formulation was added to a stainless steel pot. With constant mixing, the formulation temperature was raised to 138° C. The pot was then removed from the heat, allowing cool to 120° C. and 0.7 g of flavor containing the ingredients in equal amounts: benzaldehyde, tolyl aldehyde, ethyl acetate, maltol, Davana oil, methyl heptinyl carbonate and 3 g of citric acid was added. The resulting cherry flavored liquid candy was then deposited into molds, and the molds containing the liquid candy were cooled to room temperature, yielding 600 g of finished hard candy. The resulting control candy exhibited a green, candied type of flavor without exhibiting any cooling effect. A test candy was further prepared using the above recipe modified by adding 0.18 g of 1-(2-isopropyl-5-methyl-cyclohexyl)-4-(pyrrolidine-1-carbonyl)-pyrrolidin-2-one (Structure VI, 300 ppm) or 1-(2-isopropyl-5-methyl-cyclohexyl)-4-(piperidine-1-carbonyl)-pyrrolidin-2-one (Structure VII, 300 ppm). The resulting test candies had a taste profile substantially identical to that of the control candy; however the test candies further exhibited substantial cooling effect as described below:

EXAMPLE XV (Continued)

| Group | Profile |
|---|---|
| Control Candy | Exhibited a green, candied type of flavor without cooling. |
| Structure VI-containing Gum (300 ppm) | At 0-1 minute: cooling with slight bitterness;<br>At 1-3 minutes: cooling built up;<br>At 3-5 minutes: cooling on the roof of mouth;<br>At 5-10 minutes: cooling with some bitterness;<br>At 10-20 minutes: cooling with mild bitterness;<br>At 20-30 minutes: cooling remained. |
| Structure VII-containing Gum (300 ppm) | At 0-1 minute: bitterness;<br>At 1-3 minutes: cooling breath, strong cooling;<br>At 3-5 minutes: intense cooling;<br>At 5-10 minutes: intense cooling throughout mouth;<br>At 10-20 minutes: very strong cooling, almost burning;<br>At 20-30 minutes: strong and lasting cooling. |

What is claimed is:

1. A compound of Formula I:

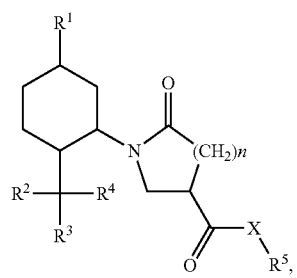

Formula I wherein n is an integer of 1;

$R^1$, $R^2$ and $R^3$ are each methyl;

$R^4$ is hydrogen or methyl;

X is nitrogen;

$R^5$ is a $C_1$-$C_7$ alkyl;

or $R^5$ together with X form a N-linked, saturated 3- to 8-membered heterocyclic ring.

2. The compound of claim 1, wherein the compound is selected from the group consisting of:

4-(azetidine-1-carbonyl)-1-(2-isopropyl-5-methyl-cyclohexyl)-pyrrolidin-2-one;

1-(2-isopropyl-5-methyl-cyclohexyl)-4-(pyrrolidine-1-carbonyl)-pyrrolidin-2-one;

1-(2-isopropyl-5-methyl-cyclohexyl)-4-(piperidine-1-carbonyl)-pyrrolidin-2-one;

4-(azepane-1-carbonyl)-1-(2-isopropyl-5-methyl-cyclohexyl)-pyrrolidin-2-one;

1-(2-methyl-cyclohexyl)-5-oxo-pyrrolidine-3-carboxylic acid methyl ester;

1-(2-tert-butyl-cyclohexyl)-4-(pyrrolidine-1-carbonyl)-pyrrolidin-2-one; and
1-(2-tert-butyl-cyclohexyl)-4-(piperidine-1-carbonyl)-pyrrolidin-2-one.

3. A flavor composition comprising an olfactory effective amount of a compound of Formula I and an inert diluent or carrier:

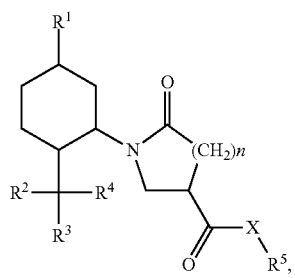

Formula I wherein n is an integer of 1;
$R^1$, $R^2$ and $R^3$ are each methyl;
$R^4$ is hydrogen or methyl;
X is nitrogen;
$R^5$ is a $C_1$-$C_7$ alkyl;
or $R^5$ together with X form a N-linked, saturated 3- to 8-membered heterocyclic ring.

4. The flavor composition of claim 3, wherein the compound is selected from the group consisting of:
  4-(azetidine-1-carbonyl)-1-(2-isopropyl-5-methyl-cyclohexyl)-pyrrolidin-2-one;
  1-(2-isopropyl-5-methyl-cyclohexyl)-4-(pyrrolidine-1-carbonyl)-pyrrolidin-2-one;
  1-(2-isopropyl-5-methyl-cyclohexyl)-4-(piperidine-1-carbonyl)-pyrrolidin-2-one;
  4-(azepane-1-carbonyl)-1-(2-isopropyl-5-methyl-cyclohexyl)-pyrrolidin-2-one;
  1-(2-methyl-cyclohexyl)-5-oxo-pyrrolidine-3-carboxylic acid methyl ester;
  1-(2-tert-butyl-cyclohexyl)-4-(pyrrolidine-1-carbonyl)-pyrrolidin-2-one; and
  1-(2-tert-butyl-cyclohexyl)-4-(piperidine-1-carbonyl)-pyrrolidin-2-one.

5. A foodstuff comprising an olfactory effective amount of the flavor composition of claim 3.

6. The foodstuff of claim 5, wherein the compound is selected from the group consisting of:
  4-(azetidine-1-carbonyl)-1-(2-isopropyl-5-methyl-cyclohexyl)-pyrrolidin-2-one;
  1-(2-isopropyl-5-methyl-cyclohexyl)-4-(pyrrolidine-1-carbonyl)-pyrrolidin-2-one;
  1-(2-isopropyl-5-methyl-cyclohexyl)-4-(piperidine-1-carbonyl)-pyrrolidin-2-one;
  4-(azepane-1-carbonyl)-1-(2-isopropyl-5-methyl-cyclohexyl)-pyrrolidin-2-one;
  1-(2-methyl-cyclohexyl)-5-oxo-pyrrolidine-3-carboxylic acid methyl ester;
  1-(2-tert-butyl-cyclohexyl)-4-(pyrrolidine-1-carbonyl)-pyrrolidin-2-one; and
  1-(2-tert-butyl-cyclohexyl)-4-(piperidine-1-carbonyl)-pyrrolidin-2-one.

7. The foodstuff of claim 6, wherein the compound is 1-(2-isopropyl-5-methyl-cyclohexyl)-4-(pyrrolidine-1-carbonyl)-pyrrolidin-2-one, and wherein the foodstuff is selected from the group consisting of a chewing gum and a hard candy.

8. The foodstuff of claim 6, wherein the compound is 4-(azepane-1-carbonyl)-1-(2-isopropyl-5-methyl-cyclohexyl)-pyrrolidin-2-one, and wherein the foodstuff is selected from the group consisting of a chewing gum and a hard candy.

9. The flavor composition of claim 3, wherein the compound is provided at a level of greater than about 1 ppb by weight.

10. The flavor composition of claim 3, wherein the compound is provided at a level of from about 0.1 to about 10,000 ppm by weight.

11. The flavor composition of claim 3, wherein the compound is provided at a level of from about 50 to about 5000 ppm by weight.

12. A method of augmenting, enhancing or imparting cooling effect to a material selected from the group consisting of foodstuff, a medicinal product, and a cosmetic product comprising the step of incorporating an olfactory acceptable amount of a compound of Formula I:

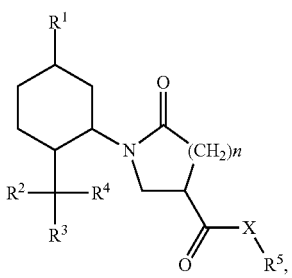

Formula I wherein n is an integer of 1 or 2; $R^1$, $R^2$, $R^3$, and $R^4$ are each independently selected from the group consisting of hydrogen and methyl;
X is selected from the group consisting of oxygen and nitrogen; and
$R^5$ is hydrogen or a $C_1$-$C_7$ linear or branched acyclic hydrocarbon group, or $R^5$ together with X form a 3- to 8-membered heterocyclic hydrocarbon group.

13. The method of claim 12, wherein the compound is selected from the group consisting of:
  1-(2-isopropyl-5-methyl-cyclohexyl)-5-oxo-pyrrolidine-3-carboxylic acid methyl ester;
  1-(2-isopropyl-5-methyl-cyclohexyl)-5-oxo-pyrrolidine-3-carboxylic acid;
  1-(2-isopropyl-5-methyl-cyclohexyl)-5-oxo-pyrrolidine-3-carboxylic acid isobutyl-amide;
  1-(2-isopropyl-5-methyl-cyclohexyl)-5-oxo-pyrrolidine-3-carboxylic acid ethyl-methyl-amide;
  4-(azetidine-1-carbonyl)-1-(2-isopropyl-5-methyl-cyclohexyl)-pyrrolidin-2-one;
  1-(2-isopropyl-5-methyl-cyclohexyl)-4-(pyrrolidine-1-carbonyl)-pyrrolidin-2-one;
  1-(2-isopropyl-5-methyl-cyclohexyl)-4-(piperidine-1-carbonyl)-pyrrolidin-2-one;
  4-(azepane-1-carbonyl)-1-(2-isopropyl-5-methyl-cyclohexyl)-pyrrolidin-2-one;
  1-(2-methyl-cyclohexyl)-5-oxo-pyrrolidine-3-carboxylic acid methyl ester;
  1-(2-tert-butyl-cyclohexyl)-4-(pyrrolidine-1-carbonyl)-pyrrolidin-2-one;
  1-(2-tert-butyl-cyclohexyl)-4-(piperidine-1-carbonyl)-pyrrolidin-2-one;

1-(2-isopropyl-5-methyl-cyclohexyl)-5-(pyrrolidine-1-carbonyl)-piperidin-2-one; and 1-(2-isopropyl-5-methyl-cyclohexyl)-5-(piperidine-1-carbonyl)-piperidin-2-one.

14. The method of claim 13, wherein the material is the foodstuff selected from the group consisting of a chewing gum and a hard candy, and wherein the compound is 1-(2-isopropyl-5-methyl-cyclohexyl)-4-(pyrrolidine-1-carbonyl)-pyrrolidin-2-one.

15. The method of claim 13, wherein the material is the foodstuff selected from the group consisting of a chewing gum and a hard candy, and wherein the compound is 4-(azepane-1-carbonyl)-1-(2-isopropyl-5-methyl-cyclohexyl)-pyrrolidin-2-one.

* * * * *